(12) United States Patent
Girard et al.

(10) Patent No.: US 9,333,026 B2
(45) Date of Patent: May 10, 2016

(54) RADIO FREQUENCY LASSO

(75) Inventors: Mark E. Girard, Medway, MA (US); Tom Casey, Grafton, MA (US); Kimbolt Young, Newtonville, MA (US); Nathan Murphy, South Boston, MA (US); Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2241 days.

(21) Appl. No.: 11/282,928

(22) Filed: Nov. 18, 2005

(65) Prior Publication Data

US 2007/0118110 A1    May 24, 2007
US 2007/0270796 A2    Nov. 22, 2007

(51) Int. Cl.
*A61B 18/14*    (2006.01)

(52) U.S. Cl.
CPC ........... *A61B 18/14* (2013.01); *A61B 2018/143* (2013.01); *A61B 2018/1407* (2013.01); *A61B 2018/1432* (2013.01); *A61B 2018/1475* (2013.01)

(58) Field of Classification Search
CPC ................. A61B 2018/1407; A61B 2018/141; A61B 2018/143; A61B 2018/1432; A61B 2018/1475; A61B 18/14
USPC .................... 606/41, 42, 45, 48, 113
See application file for complete search history.

(56) References Cited

U.S. PATENT DOCUMENTS

| 3,901,242 | A | * | 8/1975 | Storz ................................ 606/46 |
| 5,855,576 | A |   | 1/1999 | LeVeen et al. |
| 5,910,129 | A |   | 6/1999 | Koblish et al. |
| 6,050,995 | A | * | 4/2000 | Durgin ............................ 606/47 |
| 6,080,149 | A |   | 6/2000 | Huang et al. |
| 6,517,538 | B1 | * | 2/2003 | Jacob et al. .................... 606/47 |

(Continued)

FOREIGN PATENT DOCUMENTS

WO      WO 99/18878      4/1999

OTHER PUBLICATIONS

International Preliminary Report on Patentability (Chapter I of the Patent Cooperation Treaty) for PCT/US2006/060255, Applicant: Boston Scientific Scimed, Inc., Form PCT/IB/326, dated May 29, 2008 (8 pages).

(Continued)

*Primary Examiner* — Michael Peffley
*Assistant Examiner* — Samantha Good
(74) *Attorney, Agent, or Firm* — Bookoff McAndrews, PLLC

(57) ABSTRACT

A system for resecting tissue includes a loop structure configured for cutting tissue, at least a portion of the loop structure formed by an elongate structure having a first end and a second end, wherein a length of the loop structure is adjustable by positioning the first end relative to the second end, wherein a first portion of the loop structure comprises a first electrode, and a second portion of the loop structure comprises a second electrode. A system for resecting tissue includes a loop structure configured for cutting tissue, the loop structure formed by an elongate structure having a first end and a second end, wherein a length of the loop structure is adjustable by positioning the first end relative to the second end, and a support structure coupled to a portion of the elongate structure and having a surface for contacting tissue.

20 Claims, 6 Drawing Sheets

(56) References Cited

U.S. PATENT DOCUMENTS

| | | | |
|---|---|---|---|
| 6,542,781 B1 | 4/2003 | Koblish et al. | |
| 6,730,078 B2* | 5/2004 | Simpson et al. | 606/34 |
| 6,773,432 B1* | 8/2004 | Clayman et al. | 606/41 |
| 2003/0195502 A1* | 10/2003 | Garabedian et al. | 606/41 |
| 2003/0216730 A1 | 11/2003 | Barry | |
| 2005/0070895 A1* | 3/2005 | Ryan et al. | 606/48 |

OTHER PUBLICATIONS

PCT International Search Report for PCT/US2006/060255, Applicant: Boston Scientific Scimed, Inc., Form PCT/ISA/210 and 220, Aug. 28, 2007 (7 pages).

PCT Written Opinion of the International Search Authority for PCT/US2006/060255, Applicant: Boston Scientific Scimed, Inc., Form PCT/ISA/237, dated Aug. 28, 2007 (8 pages).

* cited by examiner

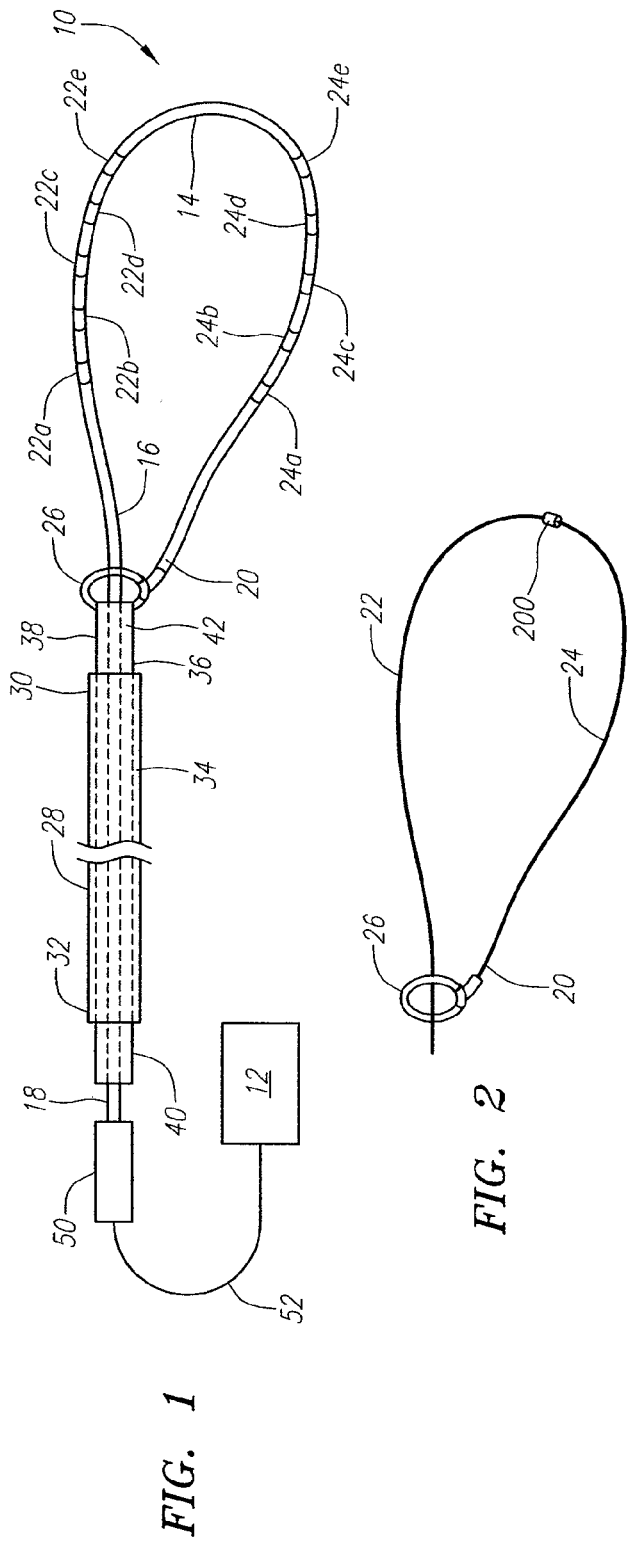
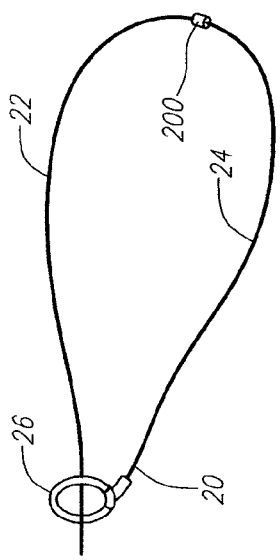
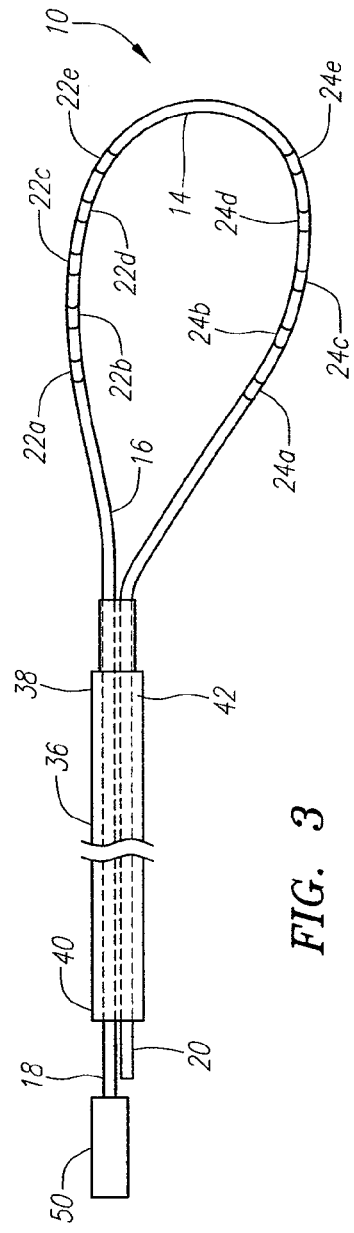
FIG. 1
FIG. 2
FIG. 3

RADIO FREQUENCY LASSO

BACKGROUND

1. Field

The field of the application relates to medical devices, and more particularly, to systems and methods for cutting and/or ablating tissue.

2. Background

Tissue may be destroyed, ablated, or otherwise treated using thermal energy during various therapeutic procedures. Many forms of thermal energy may be imparted to tissue, such as radio frequency electrical energy, microwave electromagnetic energy, laser energy, acoustic energy, or thermal conduction.

In particular, radio frequency ablation (RFA) may be used to treat patients with tissue anomalies, such as liver anomalies and many primary cancers, such as cancers of the stomach, bowel, pancreas, kidney and lung. RFA treatment involves the destroying undesirable cells by generating heat through agitation caused by the application of alternating electrical current (radio frequency energy) through the tissue.

Various RF ablation devices have been suggested for this purpose. For example, U.S. Pat. No. 5,855,576 describes an ablation apparatus that includes a plurality of wire electrodes deployable from a cannula or catheter. Each of the wires includes a proximal end that is coupled to a generator, and a distal end that may project from a distal end of the cannula. The wires are arranged in an array with the distal ends located generally radially and uniformly spaced apart from the catheter distal end. The wires may be energized in a monopolar or bipolar configuration to heat and necrose tissue within a precisely defined volumetric region of target tissue. The current may flow between closely spaced wire electrodes (bipolar mode) or between one or more wire electrodes and a larger, common electrode (monopolar mode) located remotely from the tissue to be heated.

Generally, ablation therapy uses heat to kill tissue at a target site. The effective rate of tissue ablation is highly dependent on how much of the target tissue is heated to a therapeutic level. In certain situations, complete ablation of target tissue that is adjacent a vessel may be difficult or impossible to perform, since significant blood flow may draw the produced heat away from the vessel wall, resulting in incomplete necrosis of the tissue surrounding the vessel. This phenomenon, which causes the tissue with greater blood flow to be heated less, and the tissue with lesser blood flow to be heated more, is known as the "heat sink" effect. It is believed that the heat sink effect is more pronounced for ablation of tissue adjacent large vessels that are more than 3 millimeters (mm) in diameter. Due to the increased vascularity of the liver, the heat sink effect may cause recurrence of liver tumors after a radio frequency ablation.

Also, because of the vascularity of the liver, resection of a portion of a liver (as is required by some surgeries) may result in significant bleeding. Existing techniques in managing bleeding of a resected liver include delivering embolic material within a vessel of a liver to prevent blood flow. However, such technique is time consuming, may require complex imaging modality, and may not be effective in the case in which a relatively large portion of a liver is being resected.

SUMMARY

In accordance with some embodiments, a system for resecting tissue includes a loop structure configured for cutting tissue, at least a portion of the loop structure formed by an elongate structure having a first end and a second end, wherein a length of the loop structure is adjustable by positioning the first end relative to the second end, wherein a first portion of the loop structure comprises a first electrode, and a second portion of the loop structure comprises a second electrode.

In accordance with other embodiments, a method for resecting tissue using a loop structure formed by an elongate structure having a first end and a second end, wherein a length of the loop structure is adjustable by positioning the first end relative to the second end, the method includes positioning the loop structure around a tissue structure, delivering electrical energy to a portion of the tissue structure using a circuit formed by respective first and second portions of the loop structure, and cutting the tissue structure portion by tightening the loop structure.

In accordance with other embodiments, a system for resecting tissue includes a loop structure configured for cutting tissue, the loop structure formed by an elongate structure having a first end and a second end, wherein a length of the loop structure is adjustable by positioning the first end relative to the second end, and a support structure coupled to a portion of the elongate structure and having a surface for contacting tissue.

In accordance with other embodiments, a method for resecting tissue using a loop structure formed by an elongate structure having a first end and a second end, wherein a length of the loop structure is adjustable by positioning the first end relative to the second end, the elongate structure coupled to a support structure that forms a part of the loop structure, the method includes positioning the support structure under a tissue structure, positioning the elongate structure above the tissue structure, and reducing a length of the elongate structure that is in contact with the tissue structure to thereby cut the tissue structure.

Other aspects and features of the embodiments will be evident from reading the following description of the embodiments.

BRIEF DESCRIPTION OF THE DRAWINGS

The drawings illustrate the design and utility of embodiments of the application, in which similar elements are referred to by common reference numerals. In order to better appreciate how advantages and objects of various embodiments are obtained, a more particular description of the embodiments are illustrated in the accompanying drawings. Understanding that these drawings depict only typical embodiments of the application and are not therefore to be considered limiting its scope, the embodiments will be described and explained with additional specificity and detail through the use of the accompanying drawings.

FIG. 1 illustrates a treatment system for treating tissue in accordance with some embodiments;

FIG. 2 illustrates a variation of the treatment system of FIG. 1 in accordance with other embodiments;

FIG. 3 illustrates a treatment system for treating tissue in accordance with other embodiments;

DESCRIPTION OF THE EMBODIMENTS

Figure 4A:
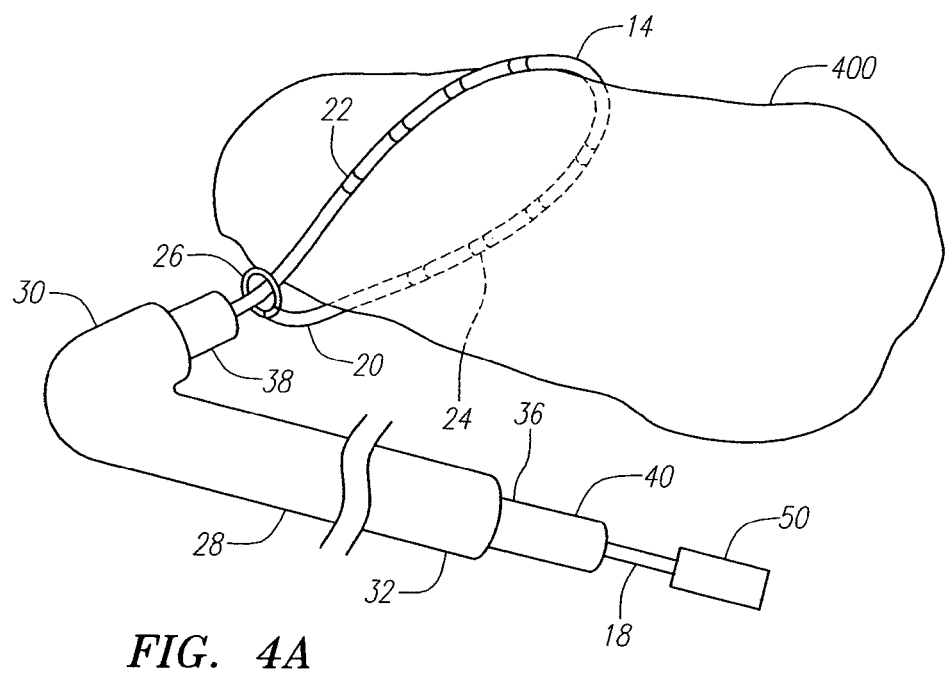
FIGS. 4A-4D illustrates a method of treating tissue using the treatment system of FIG. 1 in accordance with some embodiments.

FIG. 1 illustrates a treatment system 10 in accordance with some embodiments. The treatment system 10 includes a source of energy 12, e.g., a radio frequency (RF) generator, a loop structure 14 formed by an elongate structure 16 having a first end 18 and a second end 20, a first set of electrodes 22a-22e, and a second set of electrodes 24a-24e. The treatment system 10 further includes a cable 52 for electrically coupling the electrodes 22, 24 to energy source 12.

The generator 12 is preferably capable of operating with a fixed or controlled voltage so that power and current diminish as impedance of the tissue being ablated increases. Exemplary generators are described in U.S. Pat. No. 6,080,149, the disclosure of which is expressly incorporated by reference herein. The preferred generator 12 may operate at relatively low fixed voltages, typically below one hundred fifty volts (150 V) peak-to-peak, and preferably between about fifty and one hundred volts (50-100 V). Such radio frequency generators are available from Boston Scientific Corporation, assignee of the present application, as well as from other commercial suppliers. It should be noted that the generator 12 is not limited to those that operate at the range of voltages discussed previously, and that generators capable of operating at other ranges of voltages may also be used.

In the illustrated embodiments, the electrodes 22a-22e are electrically coupled to a first terminal of the energy source 12, and the electrodes 24a-24e are electrically coupled to a second terminal of the energy source 12. In some embodiments, the first and second terminals of the energy source 12 are opposite terminals, thereby allowing the electrodes 22, 24 to deliver energy in a bipolar mode. In this configuration, the electrodes 22a-22e form a first pole of a circuit, and the electrodes 24a-24e form a second pole of the circuit. Also, in some embodiments, the first terminal of the generator 12 may be coupled to a first control circuit (not shown) within the generator 12, that is configured to control the electrodes 22a-22e, and the second terminal of the generator 12 may be coupled to a second control circuit (not shown) within the generator 12, that is configured to control the electrodes 24a-24e. In other embodiments, each of the electrodes 22a-22e in the first set, and each of the electrodes 24a-24e in the second set can be coupled to a control circuit within the generator 12. In such cases, the control circuits can be configured (e.g., programmed, or modified by a switch) during use, such that a physician can select which of the electrodes 22a-22e and 24a-24e to be used as active electrode(s) (forming the firs pole of a circuit), and which of the electrodes 22a-22e and 24a-24e to be used as return electrode(s) (forming the second pole of a circuit). For example, in some embodiments, a physician may select electrodes 22a-22c to be active electrodes, and electrodes 22d, 22e, and 24a-24c to be return electrodes.

Although two sets of electrodes 22, 24 are shown, in other embodiments, the treatment system 10 can include other numbers of sets of electrodes. Also, in other embodiments, instead of having five electrodes in each set, the treatment system 10 can include more or less than five electrodes in each set. For example, in some embodiments, the treatment system 10 can include one electrode 22 in a first set, and one electrode 24 in a second set, with the electrodes 22, 24 being electrically insulated by an insulator 200 (FIG. 2). Each of the electrodes 22, 24 can have an elongate body, thereby extending along a substantial length of the loop structure 14. For example, in some embodiments, each of the electrodes 22, 24 can be made from a metal wire that is secured to the insulator 200. Alternatively, each of the electrodes 22, 24 can have a relatively short body, such as that shown in FIG. 1. The electrodes 22, 24 deliver ablation energy in a bipolar configuration.

In the illustrated embodiments, the treatment system 10 further includes a sheath 28 having a distal end 30, a proximal end 32, and a lumen 34 extending between the ends 30, 32. The sheath 28 can be made from a variety of materials, such as a polymer, a metal, or an alloy, and can be either rigid or flexible. As shown in the figure, at least a portion of the elongate member 16 extends through the lumen 34 of the sheath 28. During use, the loop structure 14 can be bent or stretched to a low profile, and be housed within the lumen 34 of the sheath. When the distal end 30 of the sheath 28 is positioned at a desired location (e.g., a treatment site), the loop structure 14 can then be deployed out of the lumen 34 of the sheath 28. In some embodiments, the sheath 28 has a cross sectional dimension that is small enough to allow the sheath 28 be used as a cannula. Alternatively, the sheath 28 can have other cross sectional dimensions. For example, the sheath 28 can have a cross sectional dimension that allows it be used as a trocar in an open surgery. In other embodiments, the sheath 28 is optional, and the treatment system 10 does not include the sheath 28.

As shown in FIG. 1, the treatment system 10 also includes a hollow shaft 36 having a distal end 38, a proximal end 40, and a lumen 42 extending between the ends 38, 40. The shaft 36 can be made from a variety of materials, such as a polymer, a metal, or an alloy, and can be either rigid or flexible. At least a portion of the elongate structure 16 extends through the lumen 42 of the shaft 36, with the first end 18 of the elongate structure 16 secured to a handle 50. The treatment system 10 also includes a loop 26 secured to the second end 20 of the elongate structure 16. In some embodiments, the loop 26 is secured to the distal end 38 of the shaft 36, e.g., via glue, an adhesive, or a securing device, such as a screw. In other embodiments, the loop 26 is not secured to the distal end 38, but is coupled to the distal end 38. For example, the loop 26 may be coupled to the distal end 38 by a frictional force or a bearing force.

As shown in the figure, the first end 18 of the elongate structure 16 is inserted through the loop 26, and through the lumen 42 of the shaft 36, thereby forming the loop structure 14. The length (and therefore, the size) of the loop structure 14 can be adjusted by positioning the first end 18 relative to the second end 20, or vice versa. Such can be accomplished by holding the handle 50 and the proximal end 40 of the shaft 36, and moving the handle 50 relative to the proximal end 40, or vice versa. In some cases, the size of the loop structure 14 can be increased by advancing the handle 50 (and therefore, the first end 18) distally relative to the proximal end 40 (and therefore, the second end 20). Alternatively, the size of the loop structure 14 can be decreased by retracting the handle 50 proximally relative to the proximal end 40.

In other embodiments, the treatment system 10 does not include the loop 26. In such cases, the second end 20 of the elongate member 16 is secured to the distal end 38 of the shaft 36 using, for example, a glue, an adhesive, or a securing device, such as a screw. In further embodiments, the shaft 36 and the elongate structure 16 can be made from the same member. In such cases, a portion of the distal end 38 of the shaft 36 extends to form a portion of the second end 20 of the elongate structure 16.

In other embodiments, the loop structure 14 can have different configurations. For example, in other embodiments, the loop structure 14 can be formed by inserting both ends 18, 20 of the elongate member 16 through the shaft 36 (FIG. 3). The length (and therefore, the size) of the loop structure 14 can be adjusted by positioning the first end 18 relative to the second end 20, or vice versa. For example, the size of the loop structure 14 can be increased by advancing the first end 18 (e.g., using the handle 50) distally relative to the second end 20. Alternatively, the size of the loop structure 14 can be decreased by retracting the first end 18 proximally relative to the second end 20.

Figure 10:
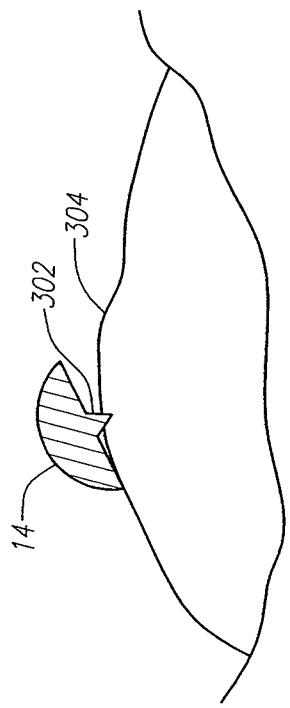
FIG. 10 illustrates a cross section of a lasso in accordance with some embodiments.

In any of the embodiments of the treatment system 10 described herein, the loop structure 14 can have a feature that allows the loop structure 14 be used as a tissue cutting device. For example, in some embodiments, the loop structure 14 can have a cross sectional dimension that is sufficiently small (such as, less than 2 millimeters (mm), or more preferably, less than 1 mm) to allow the loop structure 14 to cut tissue. In other embodiments, the loop structure 14 can include one or more cutting elements disposed on its surface, which allow the loop structure 14 be used to cut tissue. By means of non-limiting examples, the cutting elements can be sawteeth, diamond dusts. In other embodiments, the loop structure 14 can have a cross section which is relatively flat, thereby biasing a cutting element to be in contact with a tissue surface. For example, the loop structure 14 can have the cross sectional shape shown in FIG. 10, which biases cutting element 302 to be in contact with tissue surface 304. The cutting element 302 has a sharp end that can assist focusing energy (e.g., radio frequency energy) towards a direction, thereby providing an "edge effect." In further embodiments, the loop structure 14 has a size and/or cross sectional profile that does not allow the loop structure 14 to cut tissue.

FIGS. 4A-4D illustrate a method of treating tissue using the treatment system 10 of FIG. 1 in accordance with some embodiments. First, the loop structure 14 is delivered to a target site, and the loop structure 14 is placed around a tissue 400 (FIG. 4A).

Various techniques can be used to deliver the loop structure 14 to the target site. In some embodiments, an incision is made on a patient's skin to create an opening. The loop structure 14 is then inserted through the opening percutaneously. In some cases, if the treatment system 10 includes the sheath 28, the sheath 28 can be inserted partially through the skin opening, and the loop structure 14 is then inserted into the lumen 34 of the sheath 28 to gain access to the target site. Alternatively, the distal end 38 of the shaft 36 can be inserted into a vessel, and is then steered to the target site. In such cases, the treatment system 10 can further include a steering mechanism for steering the distal end 38 of the shaft 36. For example, the treatment system 10 can include one or more steering wires that are secured to the distal end 38. Alternatively, the treatment system 10 can include a guidewire for steering the distal end 38. Steering mechanisms are well known in the art, and therefore, would not be described in detail. In some cases, the distal end 38 of the shaft 36 can have a sharp tip for allowing the distal end 38 to puncture a vessel. Such configuration allows the distal end 38 to reach target tissue that is outside a vessel.

In the illustrated embodiments, before the loop structure 14 is placed at the target site, the loop structure 14 (or the elongate structure 16) is housed within the lumen 42 of the shaft 36, and is bent or stretched to a low profile. In some embodiments, the elongate structure 16 which forms the loop structure 14 is stretched to have a profile that resembles the profile of the shaft 36. As such, the loop structure 14 may or may not have a loop configuration when confined within the lumen 42 of the shaft 36. After the distal end 38 is positioned at a desired position, the first end 18 of the elongate structure 16 is advanced distally to thereby deploy the elongate structure 16 out of the distal end 38 of the shaft 42, placing the loop structure 14 adjacent the tissue 400 to be treated.

As shown in FIG. 4A, after the loop structure 14 is deployed or formed, the loop structure 14 is placed around the tissue 400. The first end 18 is then retracted proximally relative to the second end 20 to tighten the loop structure 14 around the tissue 400. As a result, the electrodes 22, 24 are placed against surface of the tissue 400.

Figure 4B:
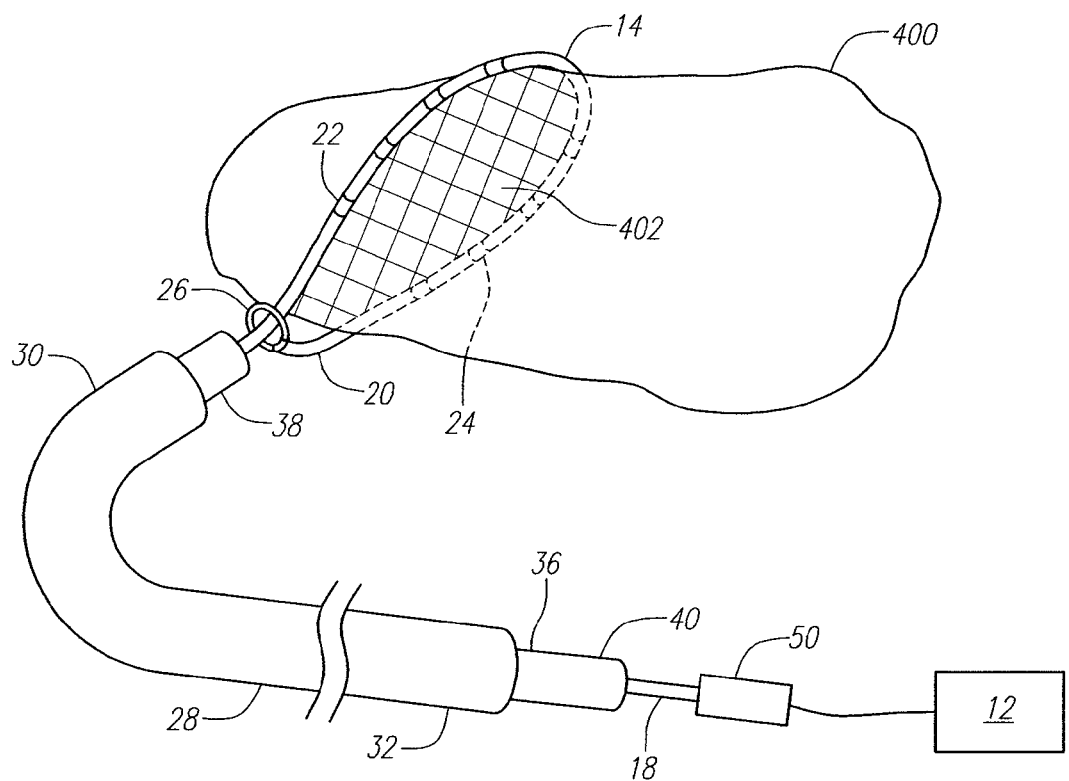

Next, energy, preferably RF electrical energy, may be delivered from the generator 12 to the first set of electrodes 22, with the second set of electrodes 24 functioning as return electrodes, thereby creating a lesion 402 between the first and second electrodes 22, 24 (FIG. 4B). Alternatively, the generator 12 may deliver energy to the second set of electrodes 24, with the first set of electrodes 22 functioning as return electrodes. In some embodiments, using the loop structure 14 to perform ablation allows most, if not all, of the cross section of the tissue 400 to be ablated. In some cases, the ablation causes blood within the ablated tissue to coagulate.

Figure 4C:
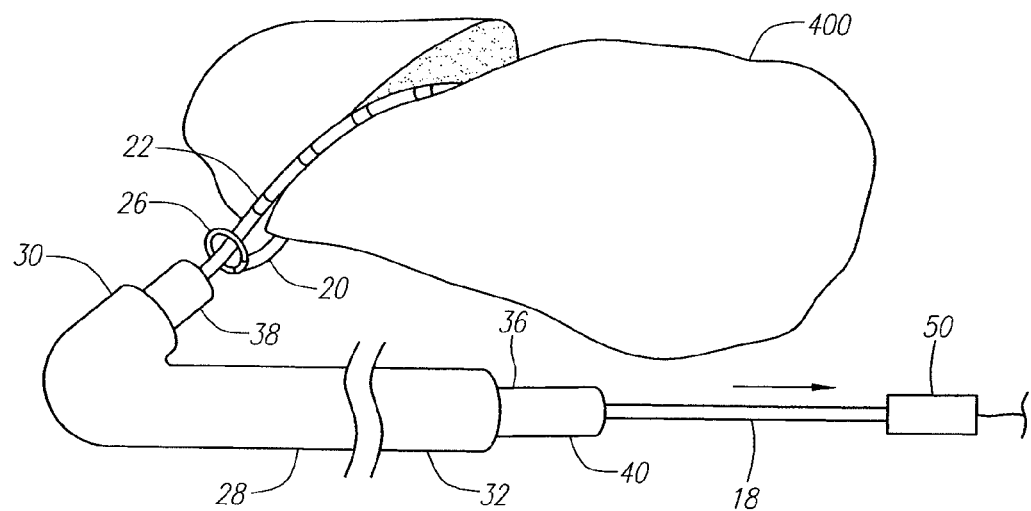
Figure 4D:
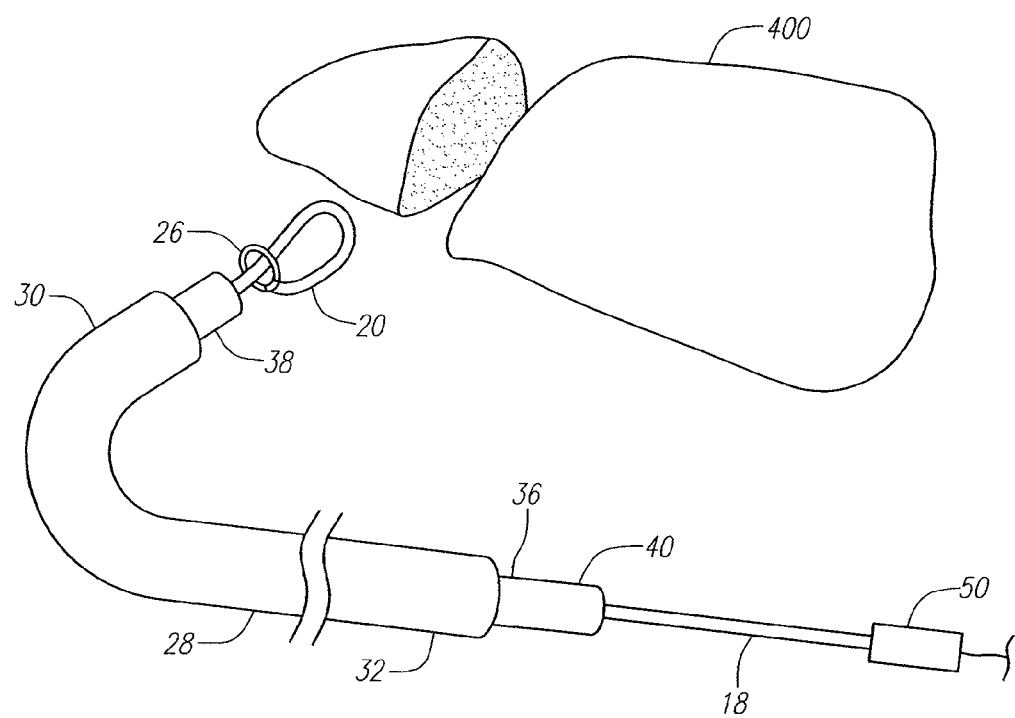

After a lesion 402 across a substantial cross section of the tissue 400 has been created, part of the tissue 400 on one side of the ablation plane can be surgically removed (resect). In the illustrated embodiments, if the loop structure 14 is capable of cutting tissue, such can be accomplished by retracting the first end 18 of the elongate member 16 proximally relative to the second end 20 to thereby reduce a size of the loop structure 14 (FIG. 4C). As the size of the loop structure 14 decreases, the loop structure 14 cuts into the tissue. The first end 18 of the elongate member 16 is continued to be positioned proximally relative to the second end 20 until the entire cross section of the tissue 400 is cut (FIG. 4D). Alternatively, if the loop structure 14 is not capable of cutting tissue, the loop structure 14 can be removed from the tissue 400, and a separate surgical device can be used to cut the tissue 400. As shown in the embodiments, because the lesion 402 is formed substantially across the entire cross section of the tissue 400, there is no or little bleeding as the tissue 400 is being cut.

In other embodiments, the ablation of the tissue 400 and the cutting of the tissue 400 can be performed simultaneously. In such cases, the electrodes 22, 24 are used to deliver ablation energy to ablate the tissue 400, while the first end 18 is positioned relative to the second end 20 to reduce the size of the loop structure 14 to cut the tissue 400 that is being ablated. In further embodiments, the ablation of the tissue 400 can be performed in a series of steps. In such cases, the size of the loop structure 14 is progressively reduced after each step of the ablation. For example, tissue adjacent surface of organ 400 can be initially ablated first, and is then cut using the loop structure 14. Additional tissue further below the surface of the organ 400 is then ablated, and is cut using the loop structure 14 after the ablation. Such is repeated until a resection is made across an entire cross section of the organ 400.

In other embodiments, instead of cutting the tissue 400, after the lesion 402 has been created, the treatment system 10 (or another ablation device/system) can be used to ablate a target treatment site (e.g., a tumor) located on one side of the lesion 402. In such cases, the formed lesion 402 can be used as a barrier to prevent or reduce blood from flowing from one side of the lesion 402 to the other side of the lesion 402, thereby allowing the target treatment site located on one side of the lesion 402 to be ablated efficiently without being affected by a heat sink effect due to blood flow. In some embodiments, the loop structure 14 can be tightened around the tissue 400 to compress a cross section, thereby preventing or reducing blood flow across the cross section of the tissue 400.

Figure 5:
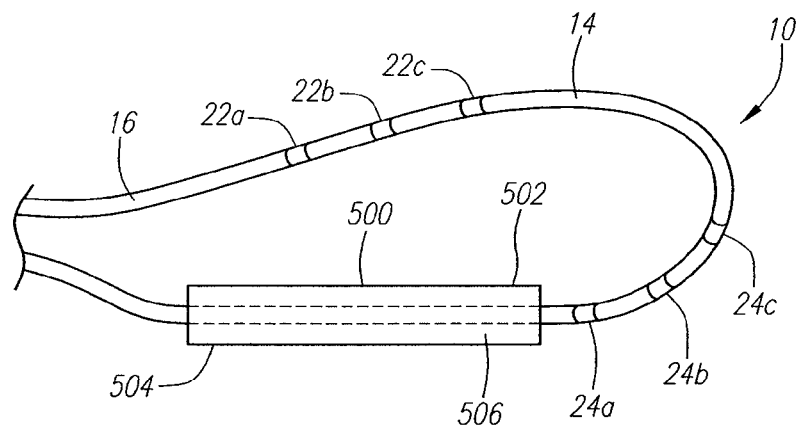
FIG. 5 illustrates a treatment system for treating tissue in accordance with other embodiments, showing the treatment system having a support structure.

In any of the embodiments described herein, the treatment system 10 can further include a support structure 500 (FIG. 5). During use, the support structure 500 is placed against tissue surface on one side of the tissue, and supports the tissue while the loop structure 14 is used to cut the tissue from another side of the tissue. As such, the support structure 500 is sized and/or shaped such that it does not cut through tissue. In the illustrated embodiments, the support structure 500 includes a first end 502, a second end 504, and a lumen 506 extending between the ends 502, 504. A portion of the loop structure 14 is housed within the lumen 506 of the support structure 500. In other embodiments, the support structure 500 does not have the lumen 506. In such cases, a first portion of the elongate structure 16 is secured to one side of the support structure 500, and a second portion of the elongate structure 16 is secured to another side of the support structure 500, thereby allowing the support structure 500 to form a part of the loop structure 14. In further embodiments, the support structure 500 can include one or more anchoring elements disposed on a surface of the support structure 500. The anchoring element(s) pierces into tissue to thereby prevent the support structure 500 from sliding relative to a tissue surface. By means of non-limiting examples, the anchoring element can be a pin, a hook, or any of other devices that can penetrate into tissue.

Figure 6:
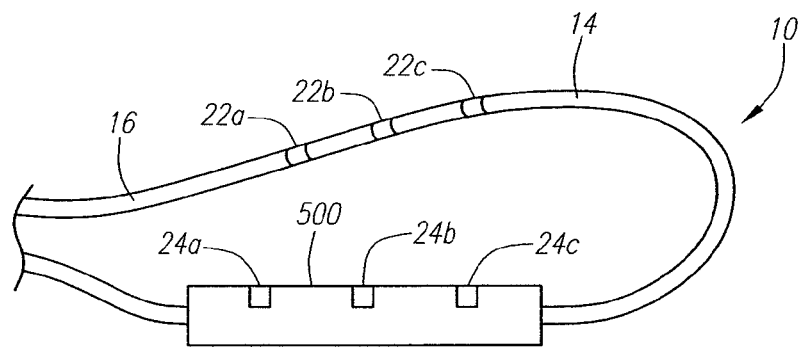
FIG. 6 illustrates a treatment system for treating tissue in accordance with other embodiments, showing the treatment system having a support structure and a plurality of electrodes on the support structure.

In other embodiments, the support structure 500 can carry one or more electrodes 24 (FIG. 6). The electrode(s) 24 can be used to perform ablation. Alternatively, the electrode(s) 24 can be used as sensing electrode(s) to sense a characteristic of tissue (e.g., temperature, impedance, etc.).

Figure 7:
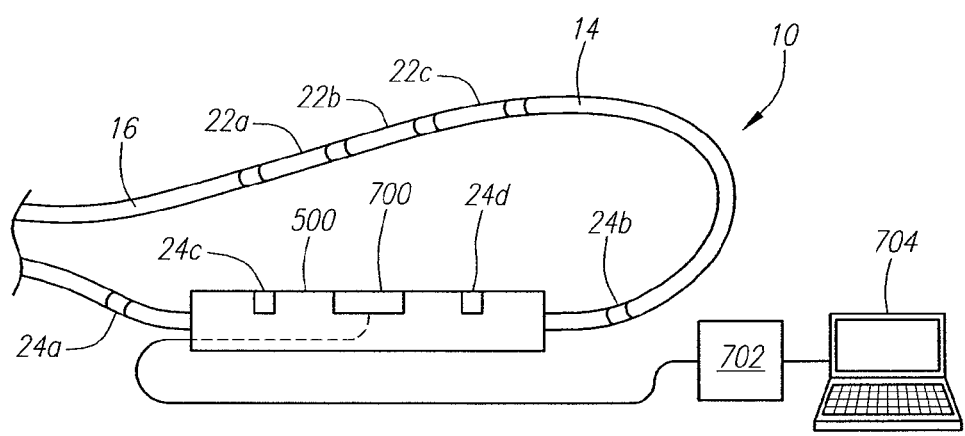
FIG. 7 illustrates a treatment system for treating tissue in accordance with other embodiments, showing the treatment system having an imaging device.

In further embodiments, any of the embodiments of the support structure 500 described herein can further include an imaging device 700 (FIG. 7). The imaging device 700 can be an ultrasound imager or any of the imaging devices known in the art. The imaging device 700 can be coupled to a processor 702 (such as a computer), which processes image data obtained by the imaging device 700, and generates graphics on a display 704 based on a result of the processing of the image data. In some embodiments, the generated graphics allow a physician to visualize tissue that is being imaged by the imaging device 700.

Figure 8B:
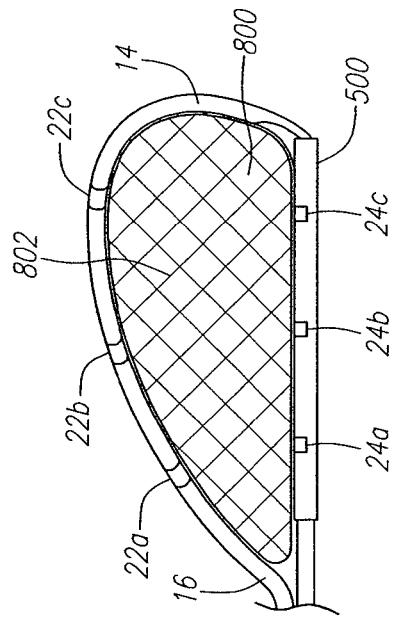
FIGS. 8A-8D illustrates a method of treating tissue using the treatment system of FIG. 6 in accordance with some embodiments.
Figure 8D:
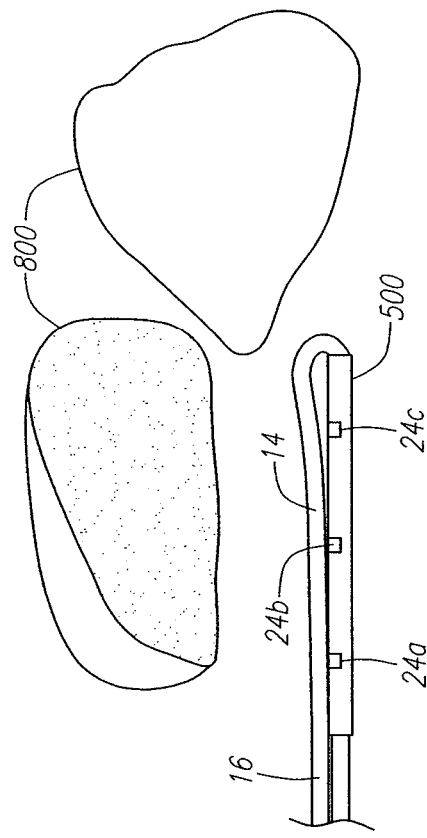
Figure 8A:
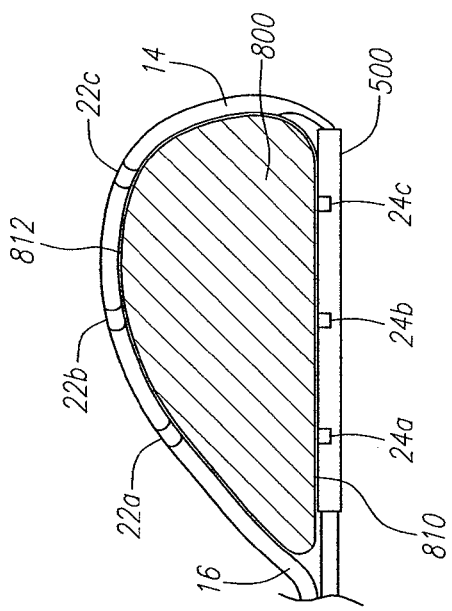

FIGS. 8A-8D illustrate a method of treating tissue using the treatment system 10 of FIG. 6 in accordance with some embodiments. First, the loop structure 14 is delivered to a target site, and the loop structure 14 is placed around a tissue 800 (FIG. 8A).

Various techniques can be used to deliver the loop structure 14 to the target site. In some embodiments, an incision is made on a patient's skin to create an opening. The loop structure 14 is then inserted through the opening percutaneously. In some cases, if the treatment system 10 includes the sheath 28, the sheath 28 can be inserted partially through the skin opening, and the loop structure 14 is then inserted into the lumen 34 of the sheath 28 to gain access to the target site. Alternatively, the distal end 38 of the shaft 36 can be inserted into a vessel, and is then steered to the target site. In such cases, the treatment system 10 can further include a steering mechanism for steering the distal end 38 of the shaft 36. For example, the treatment system 10 can include one or more steering wires that are secured to the distal end 38. Alternatively, the treatment system 10 can include a guidewire for steering the distal end 38. Steering mechanisms are well known in the art, and therefore, would not be described in detail. In some cases, the distal end 38 of the shaft 36 can have a sharp tip for allowing the distal end 38 to puncture a vessel. Such configuration allows the distal end 38 to reach target tissue that is outside a vessel.

In the illustrated embodiments, before the loop structure 14 is placed at the target site, the loop structure 14 (or the elongate structure 16) and the support structure 500 are housed within the lumen 42 of the shaft 36. In some embodiments, the elongate structure 16 which forms the loop structure 14 is stretched to have a profile that resembles the profile of the shaft 36. As such, the loop structure 14 may or may not have a loop configuration when confined within the lumen 42 of the shaft 36. Also, the support structure 500 may have a bent, compressed, or folded configuration when housed within the lumen 42 of the shaft 36. Alternatively, if the support structure 500 is made from a rigid material and is not foldable, the support structure 500 can be made sufficiently small such that it can be housed within the lumen 42. After the distal end 38 is positioned at a desired position. The first end 18 of the elongate structure 16 is advanced distally to thereby deploy the elongate structure 16 out of the distal end 38 of the shaft 42, placing the loop structure 14 adjacent tissue 800 to be treated.

As shown in FIG. 8A, after the loop structure 14 is deployed or formed, the loop structure 14 is placed around the tissue 800. The first end 18 is then retracted proximally relative to the second end 20 to tighten the loop structure 14 around the tissue 800. As a result, the electrodes 22, 24 are placed against surface of the tissue 800. In some embodiments, if the treatment system 10 includes the imaging device 700, the imaging device 700 can be used to obtain an image of a portion of the tissue 800 (e.g., to confirm placement of the loop structure 14, and/or location of target treatment area).

Next, energy, preferably RF electrical energy, may be delivered from the generator 12 to the first set of electrodes 22, with the second set of electrodes 24 functioning as return electrodes, thereby creating a lesion 802 between the first and second electrodes 22, 24 (FIG. 8B). Alternatively, the generator 12 may deliver energy to the second set of electrodes 24, with the first set of electrodes 22 functioning as return electrodes. In some embodiments, using the loop structure 14 to perform ablation allows most, if not all, of the cross section of the tissue 800 to be ablated.

Figure 8C:
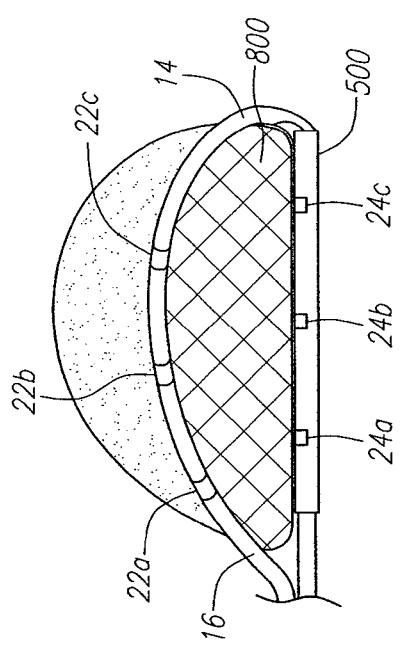

After a lesion across a substantial cross section of the tissue 800 has been created, part of the tissue 800 on one side of the ablation plane can be surgically removed (resect). In the illustrated embodiments, such can be accomplished by retracting the first end 18 of the elongate member 16 proximally relative to the second end 20 to thereby reduce a size of the loop structure 14 (FIG. 8C). As the size of the loop structure 14 decreases, the loop structure 14 cuts into the tissue 800. The first end 18 of the elongate member 16 is continued to be positioned proximally relative to the second end 20 until the entire cross section of the tissue 800 is cut (FIG. 8D). As shown in the above embodiments, the support structure 500 contacts a surface of the tissue 800 on one side 810 of the tissue 800, and does not cut through the tissue 800 from the side 810. As a result, the cutting portion of the loop structure 14 is biased to cut into the tissue 800 from side 812 of the tissue 800. In some embodiments, the support structure 500 is placed on a bottom of the tissue 800, thereby allowing a physician to visualize the top of the tissue 800 as the loop structure 14 is used to cut into the tissue 800 from the top side. Also, as shown in the embodiments, because the lesion 802 is formed substantially across the entire cross section of the tissue 800, there is no or little bleeding as the tissue 400 is being cut.

In other embodiments, the ablation of the tissue 800 and the cutting of the tissue 800 can be performed simultaneously. In such cases, the electrodes 22, 24 are used to deliver ablation energy to ablate the tissue 800, while the first end 18 is positioned relative to the second end 20 to reduce the size of the loop structure 14 to cut the tissue 800 that is being ablated. In further embodiments, the ablation of the tissue 800 can be performed in a series of steps. In such cases, the size of the loop structure 14 is progressively reduced after each step of the ablation. For example, tissue adjacent surface of organ 800 can be initially ablated first, and is then cut using the loop structure 14. Additional tissue further below the surface of the organ 800 is then ablated, and is cut using the loop structure 14 after the ablation. Such is repeated until a resection is made across an entire cross section of the organ 800.

In other embodiments, instead of cutting the tissue 800, after the lesion 802 has been created, the treatment system 10 (or another ablation device/system) can be used to ablate a target treatment site (e.g., a tumor) located on one side of the lesion 802. In such cases, the formed lesion 802 can be used as a barrier to prevent or reduce blood from flowing from one side of the lesion 802 to the other side of the lesion 802, thereby allowing the target treatment site located on one side of the lesion 802 to be ablated efficiently without being affected by a heat sink effect due to blood flow.

In the above embodiments, the electrodes 22, 24 are used to perform tissue ablation in a bipolar configuration. Alternatively, the electrodes 22, 24 can be used to perform tissue ablation in a monopolar configuration. In such cases, the electrodes 22, 24 may be connected to an active terminal of the generator 12, and a common ground pad electrode (not shown) is electrically coupled to a return terminal of the generator 12. The electrodes 22, 24 then deliver energy to the common ground pad electrode, which is generally placed on a patient's skin, in a monopolar mode.

Also, in any of the embodiments described herein, the treatment system 10 may not include the electrodes 22, 24 and the energy source 12. For example, in other embodiments, the system 10 of FIG. 5, does not include the electrodes 22, 24. In such cases, the system 10 is only used to perform cutting or compressing of tissue.

Figure 9:
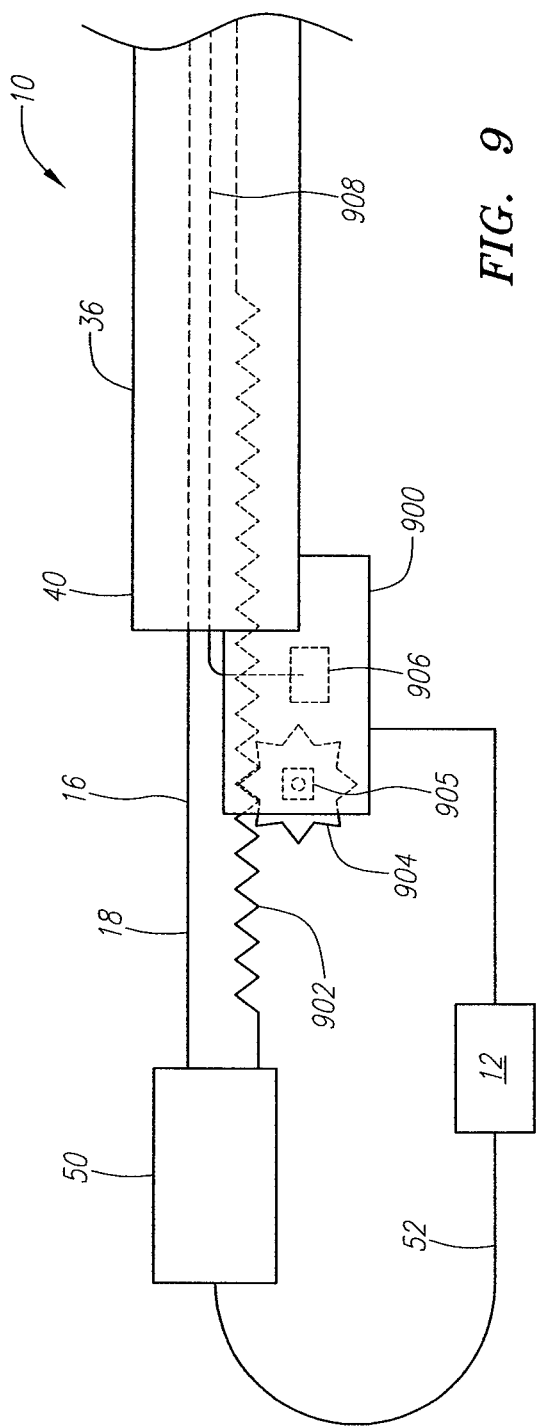
FIG. 9 illustrates a variation of the treatment system of FIG. 1 in accordance with other embodiments.

In any of the embodiments described herein, the treatment system 10 can further include a positioner 900 coupled to the elongate structure 16 (FIG. 9). In such cases, the elongate structure 16 has a plurality of teeth 902, which allows a gear 904 driven by a motor 905 in the positioner 900 to position the elongate structure 16 relative to the shaft 36. In the illustrated embodiments, the positioner 900 further includes a processor 906, and a signal wire 908 for supplying signals from a sensing electrode (not shown) on the loop structure 14 to the processor 906. During use, the sensing electrode senses a characteristic, such as temperature or impedance, of tissue being ablated, and the wire 908 transmits a signal associated with the sensed characteristic to the processor 906. The processor 906, in turn, actuates the motor 905 to cause the gear 904 to turn in response to the signal received from the sensing electrode, thereby positioning the elongate structure 16 relative to the shaft 36.

In some embodiments, the received signal indicates that tissue in contact with the sensing electrode has been desirably ablated. For example, the processor 906 can be configured to compare the received signal (e.g., impedance) with a prescribed value, and determine that the tissue has been desirably ablated if the signal exceeds the prescribed value. In such cases, the positioner 900 will causes the shaft 16 to move proximately relative to the shaft 36 by a prescribed increment, thereby reducing the size of the loop of the loop structure 14 to cut tissue. The ablation procedure is then repeated to ablate additional tissue. When the additional tissue is desirably ablated, as indicated by the impedance signal received by the processor 906, the processor 906 again causes the dimension of the loop structure 14 to further reduce, thereby further cutting into the tissue that has been ablated. The above is repeated until the entire target tissue has been cut by the loop structure 14.

In other embodiments, instead of having the motor 905, unit 900 is an instruction device that includes a signaling device (not shown), such as an alarm or a LED light. In such cases, the instruction device 900 does not include the gear 904. During use, the processor 906 receives signal from the sensing electrode, and activates the signaling device when the signal indicates that tissue in contact with the sensing electrode has been desirably ablated. For example, in the case of the signaling device being an alarm, the processor 906 activates the signaling device to emit an audio signal, thereby instructing a physician to position the handle 50 proximately by a prescribed increment. As a result the loop size of the loop structure 14 is reduced to cause the loop structure 14 to cut into tissue. The ablation procedure is then repeated to ablate additional tissue. The above is repeated until the entire target tissue has been cut by the loop structure 14.

It should be noted that the treatment system 10 is not necessarily limited to the configurations described previously, and that the treatment system 10 can have other configurations in other embodiments. For example, in other embodiments, the electrode(s) 22 and the electrode(s) 24 can have different shapes and/or sizes. Also, in other embodiments, instead of having the electrodes 22, 24 for delivering RF energy, the treatment system 10 can include other types of energy delivering devices. For example, in other embodiments, the treatment system 10 can include one or more ultrasound transducers (for generating ultrasound energy), or one or more microwave energy generators (for generating microwave energy), that are located on, or form part of, the loop structure 14.

In any of the embodiments described herein, instead of looping around target tissue to cut tissue from its perimeter, the treatment system 10 can be used to resect tissue from within the tissue. For example, the distal end 38 can be placed adjacent to tissue surface, and the loop structure 14 is then deployed out of the distal end 38 to cut into tissue. As the loop structure 14 is further deployed, it cut closer and closer to a tissue surface, until an entire cross section of the tissue is resect. In such cases, the loop structure 14 is made from a relatively rigid material that allows the loop structure 14 to cut into tissue as the loop structure 14 is deployed out from the distal end 38.

Thus, although several embodiments have been shown and described, it would be apparent to those skilled in the art that many changes and modifications may be made thereunto without the departing from the scope of the invention, which is defined by the following claims and their equivalents.

What is claimed:

1. A system for resecting tissue, comprising:
a loop structure having a cutting portion configured for cutting tissue, at least a portion of the loop structure formed by an elongate structure having a proximal end and a distal end, wherein a length of the loop structure is adjustable by adjusting a position of the proximal end relative to a position of the distal end, wherein a loop is fixedly secured to the distal end of the elongate structure, and wherein a portion of the elongate structure is inserted through the loop;
a positioner for automatically reducing the loop size of the loop structure and cutting tissue with the cutting portion, wherein the positioner automatically reduces the loop size in response to a received signal; and
wherein a first portion of the loop structure comprises a plurality of electrodes including a first electrode, and a second portion of the loop structure comprises a second electrode.

2. The system of claim 1, further comprising a sheath for housing at least a portion of the loop structure.

3. The system of claim 1, further comprising an electrical energy generator, wherein the first electrode is electrically coupled to a first terminal of the generator, and the second electrode is electrically coupled to a second terminal of the generator, the system thereby configured to form a circuit via conduction of electrical energy through tissue between the first and second electrodes.

4. The system of claim 1, further comprising an electrode pad configured for electrically coupling to an exterior body surface, wherein the first electrode and the second electrode are electrically coupled to each other and form a first pole of a circuit, and electrode pad forms a second pole of the circuit.

5. The system of claim 1, wherein the first electrode is electrically isolated from the second electrode.

6. The system of claim 1, further comprising at least one control circuit operatively coupled to the first electrode and the second electrode.

7. The system of claim 6, wherein a first control circuit is operatively coupled to the first electrode and a second, separate control circuit is operatively coupled to the second electrode.

8. The system of claim 1, the second portion of the loop structure comprising a plurality of electrodes.

9. The system of claim 1, wherein the first electrode and the second electrode are configured in a bipolar manner.

10. The system of claim 1, wherein the first electrode and the second electrode are shaped differently.

11. The system of claim 1, wherein the first electrode and the second electrode are separated from one another by an insulator.

12. The system of claim 1, wherein the proximal end of the elongate structure comprises a plurality of teeth along a portion thereof, said positioner comprising a motor-driven gear operatively interfacing with the plurality of teeth.

13. The system of claim 12, further comprising
a sensing electrode disposed on the loop structure; and
a processor operatively coupled to the sensing electrode via a signal wire, the processor configured to operate the motor-driven gear in response to the received signal, wherein the received signal is received from the sensing electrode.

14. The system of claim 1, further comprising a shaft having a distal end and a lumen, wherein part of the elongate structure extends through the shaft lumen, and wherein the loop secured to the distal end of the elongate structure is coupled to the shaft distal end.

15. The system of claim 1, wherein the loop extends distally from a distalmost end of the elongate structure.

16. The system of claim 1, wherein the second portion of the loop structure is directly coupled to the loop, and the first portion of the loop structure is slidable through the loop.

17. A system for resecting tissue, comprising:
a loop structure having a cutting portion configured for cutting tissue, at least a portion of the loop structure formed by an elongate structure having a proximal end and a distal end, wherein a length of the loop structure is adjustable by adjusting a position of the proximal end relative to a position of the distal end, wherein a loop is fixedly secured to the distal end of the elongate structure, and wherein a portion of the elongate structure is inserted through the loop;
a positioner for automatically reducing the loop size of the loop structure and cutting tissue with the cutting portion, wherein the positioner automatically reduces the loop size in response to a received signal; and
wherein a first portion of the loop structure comprises a first electrode, and a second portion of the loop structure comprises a second electrode, wherein the first portion of the loop structure has a cross-sectional dimension that is less than a cross-sectional dimension of the second portion of the loop structure.

18. The system of claim 17, wherein the loop extends distally from a distalmost end of the elongate structure.

19. A system for resecting tissue, comprising:
a loop structure having a cutting portion configured for cutting tissue, at least a portion of the loop structure formed by an elongate structure having a proximal end and a distal end, wherein a length of the loop structure is adjustable by adjusting a position of the proximal end relative to a position of the distal end, wherein a loop is fixedly secured to the distal end of the elongate structure, and wherein a portion of the elongate structure is inserted through the loop;
a positioner for automatically reducing the loop size of the loop structure and cutting tissue with the cutting portion, wherein the positioner automatically reduces the loop size in response to a received signal; and
wherein a first portion of the loop structure comprises a first electrode, and a second portion of the loop structure comprises a second electrode, wherein the first electrode and the second electrode are configured in a monopolar manner.

20. The system of claim 19, wherein the loop extends distally from a distalmost end of the elongate structure.

* * * * *